United States Patent [19]

Albanese

[11] 4,439,344

[45] * Mar. 27, 1984

[54] WATER DISPERSIONS

[75] Inventor: James J. Albanese, House Springs, Mo.

[73] Assignee: United Industries Corporation, St. Louis, Mo.

[*] Notice: The portion of the term of this patent subsequent to Mar. 27, 2001 has been disclaimed.

[21] Appl. No.: 250,745

[22] PCT Filed: Jan. 17, 1980

[86] PCT No.: PCT/US80/00037

§ 371 Date: Sep. 2, 1980

§ 102(e) Date: Sep. 2, 1980

[87] PCT Pub. No.: WO81/01964

PCT Pub. Date: Jul. 23, 1981

[51] Int. Cl.³ .................... B01J 13/00; C08L 31/04; C08L 33/08
[52] U.S. Cl. .................... 252/312; 71/64.08; 71/DIG. 1; 106/10; 106/243; 252/11; 252/49.5; 252/311; 424/170; 424/358; 426/811; 524/230; 524/801

[58] Field of Search .............. 252/311, 312, 11, 49.5; 426/811; 71/64.08; 424/43, 45, 358, 170; 106/10, 243; 524/230, 801

[56] References Cited

U.S. PATENT DOCUMENTS

| | | | |
|---|---|---|---|
| 2,887,460 | 5/1959 | Dibert et al. | 524/245 |
| 3,039,969 | 6/1962 | Colucci et al. | 252/79 |
| 3,244,638 | 4/1966 | Foley et al. | 252/8.5 P X |
| 3,929,492 | 12/1975 | Chapman et al. | 252/305 X |

FOREIGN PATENT DOCUMENTS

| | | |
|---|---|---|
| 2427319 | 12/1975 | Fed. Rep. of Germany . |
| 2613494 | 10/1976 | Fed. Rep. of Germany . |
| 2364952 | 4/1978 | France . |
| 1026831 | 4/1966 | United Kingdom .................. 424/45 |
| 1262280 | 2/1972 | United Kingdom . |
| 1264102 | 2/1972 | United Kingdom . |
| 1533598 | 11/1978 | United Kingdom . |

*Primary Examiner*—Richard D. Lovering
*Attorney, Agent, or Firm*—Kalish & Gilster

[57] ABSTRACT

A preparation of water base character in the nature of a dispersion for providing a continuous even film or coating upon application comprising a water phase and a continuous phase wherein the active ingredient may be either water soluble or water insoluble, and including cocodiethanolamide as a dispersal agent.

15 Claims, No Drawings

WATER DISPERSIONS

DESCRIPTION

Heretofore water has not been used successfully as the carrier for numerous preparations designed to provide a continuous unbroken smooth film when applied upon a work surface. Exemplary of such preparations are rust-proofing compounds of wax, oil, or silicone bases which are currently applied in various forms utilizing non-aqueous solvents. Petrochemicals serve as the primary solvents for such compounds. Mold releases comprised of oils, animal or vegetable fats, such as lecithin or polydimethylsiloxanes constitute another example of preparations which to the present time have been applied by means of similar non-aqueous solvents. Various adhesives form a further class of compositions which have been consistently carried in other than water solvents; particularly those requiring quick tackification. A still further category is constituted of the stain-proofing compounds, especially those formed of telefluoromer resins, wherein expensive and toxic chemicals have been the solvents of choice. The foregoing merely illustrate the exceedingly wide range of preparations which have been to the present time reduced to solutions for coating application and all of which have eschewed the use of water as the carrier.

It is recognized that many active ingredients for film formation may be emulsified, but to date emulsion technology has not been satisfactory for providing a continuous film in an efficacious manner. Shortcomings of existing emulsion technology are two-fold:

(a) Those relating to oil in water have failed because the hydrophobic active ingredients must of necessity be in the oil phase and in this type of emulsion water is the continuous phase. Consequently, there is no molecular continuity of the active ingredient so that the resultant film would be discontinuous with uneven distribution of the active ingredient. An example would be the commercial silicone emulsions which are basically low viscosity polydimethylsiloxanes emulsified in water and in these emulsions the water is on the outside or in the continuous phase. Attempting to use such an emulsion as a mold release, for example, would have disappointing results because the silicone would be distributed unevenly upon the applied surface and the compound would not serve to bring about reliable mold release.

(b) Those resultant from water in oil are due to the altered nature of the active ingredient. Though the active ingredients are in the continuous phase by the nature of the present emulsion technology, these active ingredients are altered by the presence of water and/or emulsifiers and their performance is not what would be expected should such have been applied in pure form or in solvent reduction. The active ingredients as applied are altered in appearance from the pre-emulsion state. For instance, active ingredients which have been transparent become pasty or creamy; resultant applications have been disappointing. Exemplary of this would be to prepare a silicone emulsion wherein the silicone would be in the oil or continuous phase and attempt to use this as a mold release. Experience has shown that although the distribution of the silicone may be even and continuous in this type of emulsion, the presence of the water and/or emulsifiers severely limits the release effect of the silicone. These compounds simply have not worked. When applied the silicone emulsion is paste-like or creamy in appearance and not characteristic of the transparent quality of polydimethylsiloxane which would be the preferred appearance.

It is indeed apparent that the failure heretofore to utilize water as a carrier for film or coating forming agents has necessarily brought about costly development of commercial solvents with the attendant drain of fossil fuel reserves. Very few of the solvents used currently are without real or potential hazard as the same involve inherent peril factors such as caused by toxicity levels and flammability.

Therefore, it is an object of the present invention to provide a preparation which is water base and which in application is productive of a noninterrupted, continuous film with even distribution of the active ingredient; and the use of which preparation eliminates the various hazards associated with organic solvents or vehicles.

It is another object of the present invention to provide a preparation which effects the use of water as a carrier for hydrophobic chemicals, for chemicals that have previously been delivered by means of petrochemical or other non-aqueous solvents, and for improving the effectiveness of systems which presently incorporate water as a carrier.

It is a further object of the present invention to provide a preparation of the character stated which is capable of the equally efficacious application of both water soluble and water insoluble active ingredients for providing a continuous film and wherein the physical and chemical characteristics of such ingredients are unaltered from the prediluted state thereof.

It is a still further object of the present invention to provide a preparation in the nature of a dispersion which may be applied in any convenient manner to the selected work surface, such as by spraying, painting, coating, dipping, etc.

It is another object of the present invention to provide a preparation of the character stated which is of wide versatility, being capable of producing a continuous unbroken even film from a broad spectrum of film and coating agents, such as water base paints, lubricants, sealants, mold releases, protective coatings, waxes, and the like.

It is another object of the present invention to provide a preparation of the character stated which has a substantially indefinite shelf life; which may be most economically produced, there being no necessity for complex instrumentation and equipment for formulation; which is extremely effective in use; and with the films developed thereby being tenacious, durable and resistant to rupture, scuffing or the like through normal intended usage peculiar to the particular film.

DESCRIPTION OF THE INVENTION

The present invention contemplates the development of a water base preparation in the nature of a dispersion which is physically and chemically distinct from traditional emulsions and single phase solutions heretofore used for film or coating formation. The system of the present invention embodies immiscible phases, one of which may be considered a continuous or oil phase, and the other a water phase, with there being a novel dispersal agent for effecting the dispersion of these two phases. By reason of the inclusion of this dispersal agent water is rendered effective as a carrier for hydrophobic active ingredients as well as for water soluble chemicals; the latter necessarily being also soluble in the continuous phase. The preparations of this invention are amenable to application in any conventional manner and thus may be applied upon the preselected surface as by spraying, painting, dipping and the like, but with the resultant film being uninterrupted by any lacunae, pores or geometric formations and with the active ingredient being evenly distributed.

Although the constituents of the preparation will be discussed in greater detail below, attention is directed to the unique dispersal agent which is critical for the development of preparations of this invention. It has been found that a specific cocodiethanolamide from that class of chemicals, which has been heretofore recognized as emulsifiers, possesses certain unexpected and surprising properties when used in a predetermined proportionality in the two phase system of the present invention. This particular cocodiethanolamide is an amber liquid having a congealing point of approximately 6° C. and with a specific gravity at 25% C. of 0.99. The free or unreacted fatty acid, as lauric, is 3%-4% maximum and the pH of a 1% dispersion is between 8 and 9. This compound is soluble in alcohols, glycols, ketones, esters, aromatic and aliphatic hydrocarbons, and chlorinated solvents, while also being dispersible in water at low concentrations of 1 to 2%. It is also soluble at higher concentrations and with a 10% solution being quite viscous approximating a gel.

It is to be thus understood that the term "cocodiethanolamide" as referred to and described herein shall be that form of the compound possessing the above-described physical and chemical characteristics.

It has been discovered that providing cocodiethanolamide in an amount approximating 0.5% by weight of the system or preparation will react with the water phase and the active ingredient phase when it is not in an emulsion to bring about what is generally considered an unstable emulsion, that is, wherein the phases tend to separate, but are capable of being brought into relative stability by agitation, and upon application the phases separate and revert to their constituent components whereby the active ingredient does not produce a continuous film but one which is highly irregular and interrupted, typical of the results obtained to the present time when water base solvents are utilized.

If the proportionality of the cocodiethanolamide is increased as within the range of immediately above 0.5% to approximately 2.5% by weight, when the active ingredient is initially in an unemulsified condition, a resulting stable emulsion is developed and thus the cocodiethanolamide acts in the expected manner of an emulsifying agent, so that upon dispensing of such a preparation containing such proportionality, a discontinuous broken film may be presented despite the fact that the emulsion is stable. In its generally normal state the emulsion gives a visual appearance of a homogeneous, pasty character, consistent with its being considered stable. Thus, the foregoing merely underscores that cocodiethanolamide as used in the aforesaid proportion with the active ingredients of the preparations of this invention, when such active ingredients are initially in an unemulsified condition, serves in its characteristic function as an emulsifying agent.

However, if the quantity of cocodiethanolamide is increased beyond 2.5%, as within the specific range of 2.5 to 10% by weight, the system loses its stability so that a separation immediately develops which, at first glance, would bear a seeming resemblance to the unstable emulsion incorporating a 0.5% by weight of said agent as above described. Despite any visual similarity between the phase separations of the unstable emulsion and the preparation incorporating in excess of 2.5% by weight of cocodiethanolamide, such generally cooresponding phases are quite different both chemically and physically. It is suggested that the preparation with the greater quantity of cocodiethanolamide has become a dispersion, that is atypical of traditional technology having, as stated, the immiscibility of the two phases being sharply defined. Without any intention of limitation, the preparation herein will be referred to as a "dispersion" to facilitate exposition. A continuous film is promoted by the dispersion as distinguished from the discontinuous character of the dispensing of an emulsion.

As developed more fully hereinbelow, the preferred effective range of cocodiethanolamide for preparations of the present invention is 2.5% to 3.5% by weight when the active ingredients are initially in an unemulsified condition. However, research has demonstrated that additional amounts up to 10% by weight bring about no diminution in the character and quality of the developed film. Above 10% it has been discovered that the applied coating develops an undesirable thickness of a generally lumpy character so that beyond such limit a continuous, unbroken film is no longer achievable.

This crucial, unexpected action caused by the cocodiethanolamide is all the more apparent when one recognizes that the use of emulsifying agents in emulsions cause a predictive response. It is recognized that there are numerous factors which contribute to the relative stability or instability of a particular emulsion but generally when the emulsifier is below a predetermined proportionality the associated emulsion will be in an unstable state with the phases separated. As the emulsifier is added, the emulsion becomes relatively stable, with the phases intermixing to present a homogeneous appearance; and further addition of the emulsifier generally has no effect upon the stability of the emulsion. But with the present invention the further addition of cocodiethanolamide beyond substantially 2.5% by weight of the system brings about a destruction of the erstwhile stability so that if a stable emulsion did exist, one would necessarily expect that the further addition of the cocodiethanolamide would be without effect. As pointed out, this unusual and surprising action of this particular agent supports the view that the system is no longer an emulsion with all of the various accepted emulsion characteristics but becomes a dispersion, with the cocodiethanolamide manifestly ceasing to act as an emulsifying agent. Therefore, the crucialness of this agent to preparations formed in accordance with this disclosure is apparent. It will be fully understood that no other compound has been found to possess the requisite properties despite extensive investigatory efforts.

As developed hereinabove the systems of the present invention are discussed as being in a non-emulsified state, independent of the cocodiethanolamide. However, the foregoing clearly comprehends that through the addition of the cocodiethanolamide the various systems transitorily move into an unstable emulsion, then into a stable emulsion as further cocodiethanolamide is added and then into a dispersion as the requisite energy level is achieved through the incorporation of a predetermined amount of cocodiethanolamide. Theoretically, a requisite amount of energy is manifestly required to achieve the dispersion state attained by the predetermined amount of cocodiethanolamide. Understandably, the intermediate or transitory unstable and stable states of emulsion also require respective critical energy levels. Accordingly, the present invention teaches that the specific cocodiethanolamide imparts certain characteristics to water and oil mixtures when used as described and in a quantity requisite to provide the necessary energy to exceed a stable emulsion state as such is determined in accordance with recognized technology. The extreme importance of this unique property is more fully understood when the cocodiethanolamide is added to existing stable or unstable emulsions.

It has been found that adding 0.5% by weight of cocodiethanolamide to a preparation which contains a stable emulsion is adequate to provide the necessary energy to cause such preparation to take on the unique characteristics of the dispersion of the present invention.

With preparations comprising unstable emulsions, the cocodiethanolamide must be added in a quantity sufficient to provide the necessary energy to render such emulsions stable and then to progress therebeyond to the unusual and unexpected dispersion state developed by the present invention. It is understood that the emulsified conditions of such active ingredients, that is whether the same are in stable or unstable state and to what degree, may be readily determined by well known, widely practiced technology so that as the cocodiethanolamide is added to unstable emulsions one may determine when the point of stability has been reached and then proceed with further incorporation of cocodiethanolamide to attain the dispersion with the resultant preparation having the predetermined characteristics.

It should be, of course, understood that with unstable emulsions as herein discussed, generally accepted emulsifying agents may be used for rendering such systems stable and with the cocodiethanolamide being thus added thereafter. Consequently, nothing herein is to be interpreted as requiring the use of cocodiethanolamide for raising the energy level of unstable emulsions to that of stable emulsions. The primary point is that cocodiethanolamide provides its unique functions only after the particular emulsion has reached a state of stability.

Illustrative of the foregoing is the utilization of cocodiethanolamide with latex paints which comprehend paints which are stable emulsions as well as those which have varying degrees of instability. The addition of cocodiethanolamide in an amount of no less than 0.5% to stable emulsions creates the necessary dispersion so that the particular paints are rendered amenable for preparations of this invention in conjunction with the other prerequisites of the invention. Similarly, with paints which are in unstable emulsions the addition of sufficient cocodiethanolamide to render same stable plus at least 0.5% by weight thereabove adapt same to constitute a preparation of this invention which thus may be sprayed or applied in any other convenient manner without foams, film rupture and the like and create a continuous unbroken coating or film upon the applied surface.

The foregoing clearly demonstrates that the specific emulsifiers in latex paint have provided energy that cocodiethanolamide would have had to supply to achieve a stable emulsion had such not been present. This energy is added to that of the cocodiethanolamide and with the prescribed addition thereof, as in the order of 0.5% to stable emulsions, incorporating sufficient energy to change the stable emulsions into the dispersions of the present invention.

Another example is provided by silicone emulsions* which are useful in developing a hard surface polish. Such silicone emulsions are generally stable so that the mere addition of 0.5% by weight of cocodiethanolamide will alter the character of the stable emulsion from oil in water so that the oil is now in the continuous phase. Such addition will also change the emulsion to the dispersion of the present invention so that the resultant film presented upon application of the particular preparation will be transparent and not creamy like an emulsion indicating that physical and chemical changes have occurred.

*Emulsions offered by General Electric Co. of Waterford, New York as SM2033, SM2035, etc.

However, even though the foregoing has disclosed that 0.5% of the cocodiethanolamide added to a stable emulsion will endow the preparation with attributes hitherto unachieved in this manner, the cocodiethanolamide may be added in an amount up to but not to exceed 10% and the increased amount will provide desired characteristics, such as, for instance, the degree of cohesiveness, and the particular thickness of the resultant film as may be shown, such amounts within the range of 0.5 to 10% by weight of the preparation being easily experimentally determined.

Active ingredients adapted for incorporation in preparations of the present invention may be water insoluble and comprehend the active phase of water-base paints commonly referred to as latex paints, exemplary of which are acrylic emulsions, vinyl emulsions, vinyl copolymer acetate emulsions, alkyd emulsions and polyurethane emulsions; mold release and lubricating agents, as for instance, silicones, namely the alkyl polysiloxanes and polyorganosiloxanes; lecithin and other soya or animal fat derivatives; stearates, telefluoromers, as Teflon*; also synthetic lubricants, such as butoxylated and ethoxylated glycols; as well as polybutene used for transmission belt dressing, etc.; and various common greases, such as lithium stearate, calcium stearate, petrolatum, aluminum anaphthenate, and the like for utilization as lubricant coatings; moreover, mineral seal oil, as both a penetrant and a lubricant, as well as petroleum based hydrocarbon oils and synthetic oils are amenable to incorporation in preparations of the present invention. A further category of active ingredients would be constituted of the waxes, including animal waxes, such as beeswax and stearic acid; vegetable waxes, such as carnauba, bayberry and candelilla, as well as the various artificial or synthetic waxes as obtained from distillation of paraffin base petroleum. The foregoing enumerated types and examples of active ingredients for forming constituents of preparations of this invention are not meant to be exhaustive but merely indicative of the comprehensive range of compounds which by virtue of the uniqueness of this invention may now be prepared in water borne systems to provide a continuous film which was heretofore deemed impossible.

*TEFLON is a trademark of E. I. DuPont De Nemours & Co., Inc. for tetrafluoroethylene resins.

All these compositions are of the type wherein the intended usage or purpose requires an unbroken coating.

Other active ingredients suitable for preparations of the present invention are water soluble compounds which, for purposes of illustration only, comprehend:

methoxy polyethylene glycols useful for lubricants and ointment bases for cosmetics and pharmaceuticals;

water soluble resins such as hydroxyethyl celluloses and ethylene copolymers useful for coatings, paints, adhesives, caulking compounds and for textile operations;

water soluble herbicides such as paraquat, diethanolamine salt of 2,4-dichlorophenoxy acetic acid, diethanolamine salt of 2-(2-methyl-4-chlorophenyoxy) propionic acid; and water soluble alkyl glycols and alkyl esters encompassing butoxylated and ethoxylated groups used for lubrication, hydraulic fluids, and for cosmetic and pharmaceutical applications.

Since the preparation of this invention is in the nature of a dispersion, water soluble active ingredients may be incorporated into preparations of this invention by solubilizing them in non-aqueous solvents prior to dispersal. Consequently, these active ingredients will be in the continuous or oil phase upon application. This shows the advantages of this invention for the application of water soluble active ingredients when those active ingredients, as applied in a water solution would bead up on the surface because of the surface tension of the water and consequently cause uneven distribution.

Accordingly, the range of treatments is infinite when it is recognized that such preparations can provide lubrication, mold release, adhesives, sealants, water displacement sprays, wax coatings, polymeric finishes, such as for floors and like surfaces; inks and dyes; asphaltic undercoatings, polyurethane coatings, and paints.

Additionally, the water dispersions of this invention are also readily amenable to the inclusion in the continuous or oil phase of traditional non-aqueous solvents for imparting to the resultant coating specific properties or characteristics, all in accordance with well recognized practice. Thus such solvents, in relatively small quantities as compared to the water, may be added for such purposes as film leveling, etching of the substrate, providing fragrance, and the like.

Most importantly, however, traditional non-aqueous solvents can be utilized in preparations of this invention for prediluting certain active ingredients so as to make them adaptable to the system. An example of such predilution would be certain insecticides which are solids in their pure chemical form; high viscosity oils or greases that could not be handled in a conventional manner without some dilution. Also solvents may be utilized in certain instances to protect active ingredients which are prone to hydrolysis from interfacing with the water phase and thus deteriorating. Included among such solvents are aromatic hydrocarbons, examples of which are benzene, toluene, xylene, commercial solvents which flash at 100° and 150°; aliphatics, and aliphatic petroleum napthas, such as heptane, hexane, kerosene, lacquer diluent, napthol spirits, mineral seal oil, mineral spirits, odorless mineral spirits, deodorized kerosene, pentane, petroleum ether, Stoddard solvent, textile spirits, VM&P naptha, isoparaffinic hydrocarbons, as well as mixtures and blends thereof.

Another general class of such traditional solvents are the chlorinated hydrocarbons; among the more commonly used are carbon tetrachloride; 1,1,1-trichlorethane, methylene chloride, and perchlorethylene.

In addition to the foregoing, which is not meant to suggest an exhaustive compilation of suitable solvents, there may be included tetra hydrofuran and 2-nitropropane. As indicated above, and as is implicit in the involved chemistry, the choice of solvent is made in accordance with well known considerations, such as, compatibility with the particular active ingredient, etc. Further, it is understood that such solvents may be intermixed or blended to produce a desired resultant characteristic. The blending of heptane and hexane is but illustrative in that a blend of the same would dry somewhat slower than hexane alone but faster than heptane if used alone.

Preparations of water dispersions possessing the properties of the present invention have the following general formula:

|  | PERCENT BY WEIGHT |
|---|---|
| ACTIVE INGREDIENT | Approx. .05% to 80% |
| NON-AQUEOUS SOLVENT DISPERSAL AGENT | 0 to Approx. 30% |
| Cocodiethanolamide | 2.5% to 10% |
| WATER | Approx. 10% to 97.45% |

The foregoing formulation is applicable wherein the active ingredient has not been pre-emulsified. With formulae wherein the active ingredient is in an emulsion, the following variation in the general formula would be appropriate:

|  | PERCENT BY WEIGHT |
|---|---|
| ACTIVE INGREDIENT IN EMULSION | Approx. 1% to 99.5% |
| NON-AQUEOUS SOLVENT DISPERSAL AGENT | 0 to approx. 30% |
| Cocodiethanolamide | .05% to 10% |
| WATER | 0 to Approx. 98.5% |

The application of these formulations will become more understandable as a study is made of specific formulae set forth hereinbelow.

EXAMPLE I

A preparation in the nature of a water dispersion for providing a mold release may be formulated as follows:

|  | PERCENT BY WEIGHT |
|---|---|
| ACTIVE INGREDIENT |  |
| Dimethylpolysiloxane (350 cs) | 2.0% |
| DISPERSAL AGENT |  |
| Cocodiethanolamide | 2.5% |
| WATER | 95.5% |

It will be observed that this particular formula corresponds to the first general formula above in that the active ingredient is not in an emulsion.

EXAMPLE II

Another example of a formula for providing a mold release wherein a small quantity of a non-aqueous solvent for the active ingredient is included which serves to enhance the flow or leveling characteristics of the resultant film is as follows:

|  | PERCENT BY WEIGHT |
|---|---|
| ACTIVE INGREDIENT |  |
| Dimethylpolysiloxane (350 cs) | 2.0% |

| | PERCENT BY WEIGHT |
|---|---|
| SOLVENT: | |
| Naptha | 10.0% |
| DISPERSAL AGENT | |
| Cocodiethanolamide | 2.5% |
| WATER | 85.5% |

EXAMPLE III

The following exemplifies the constitution of a water dispersion of the present invention useful as an insecticide which might be dispersed in any conventional, convenient manner such as by a hand sprayer, bulk sprayer, air gun or the like, and which will develop upon the applied surface a continuous transparent film:

| | PERCENT BY WEIGHT |
|---|---|
| ACTIVE INGREDIENT | |
| Neopynamin | 0.2% |
| D-trans-alletrin | 0.3% |
| Isopar C* | 19.5% |
| DISPERSAL AGENT | |
| Cocodiethanolamide | 2.5% |
| WATER | 77.5% |

*Isopar C is a trademark of Exxon Corporation for an isoparaffinic hydrocarbon.

It will be observed in this example that the active ingredient, although unemulsified, constitutes a solution in a petroleum distillate and with the Isopar C serving as a diluent for the associated two compounds of the active ingredient which have insecticidal properties so as to endow the same with a residual effect.

EXAMPLE IV

This example sets forth a formula for a clear transparent paint illustrating a formula which comprehends an active ingredient which has already been prediluted with a petrochemical solvent:

| | PERCENT BY WEIGHT |
|---|---|
| ACTIVE INGREDIENT | |
| Acryloid* B72 (50% dilution) | 20.0% |
| DISPERSAL AGENT | |
| Cocodiethanolamide | 3.0% |
| WATER | 77.0% |

*Acryloid is a trademark of Rohm and Haas of Philadelphia, Pennsylvania for acrylic ester resins in organic solvent solution

EXAMPLE V

The following typifies a formulation suitable for providing decorative high gloss to household plants in a safe and economical way, eliminating the problems with phytotoxicity caused by organic solvents that these leaf polishes currently employ:

| | PERCENT BY WEIGHT |
|---|---|
| ACTIVE INGREDIENT | |
| Drakeol** #7 | 2.5% |
| DISPERSAL AGENT | |
| Cocodiethanolamide | 2.5% |

| | PERCENT BY WEIGHT |
|---|---|
| WATER | 95.0% |

**Drakeol is a trademark of Pennreco Inc. of Butler, Pennsylvania for a series of white mineral oils being hydrocarbon distillates meeting the U.S.P. XV and N.F. X requirements for "petrolatum liquidum".

EXAMPLE VI

This following formula is for a preparation adapted to form a protective film upon fabrics to serve as a water/stain repellent:

| | PERCENT BY WEIGHT |
|---|---|
| ACTIVE INGREDIENT | |
| Telefluoromer resin | 0.2% |
| Acetone | 0.8% |
| SOLVENT | |
| 1,1,1-trichlorethane | 4.0% |
| DISPERSAL AGENT | |
| Cocodiethanolamide | 2.5% |
| WATER | 92.5% |

In the foregoing formula the resin has been prediluted with the acetone, while the 1,1,1-trichlorethane has been incorporated, as a solvent, for the intended purpose of thinning the resin so that the resultant film will be of desired thickness. This formula especially manifests the versatility of the present invention demonstrating the wide range of active ingredients which may be incorporated and subjected to solvents for assuring that the resultant coating or film will possess the particular attributes sought.

EXAMPLE VII

Another formula pursuant to the present invention for providing a water repellent for textiles is as follows:

| | PERCENT BY WEIGHT |
|---|---|
| ACTIVE INGREDIENT | |
| Water-proofing silicone resin | 5.0% |
| DISPERSAL AGENT | |
| Cocodiethanolamide | 2.5% |
| WATER | 92.5% |

This example also serves to reveal the extreme versatility of the present invention in that it permits the use of water to achieve water repellency.

EXAMPLE VIII

The following formula which is in accordance with the general formulation set forth above shows the application of the present invention to provide systems wherein the active ingredient is water soluble; such formula being of herbicidal character:

| | PERCENT BY WEIGHT |
|---|---|
| ACTIVE INGREDIENT | |
| Paraquat Cation | 0.2% |
| SOLVENT | |
| Odorless Mineral Spirits | 10% |
| DISPERSAL AGENT | |
| Cocodiethanolamide | 2.5% |

| | PERCENT BY WEIGHT |
|---|---|
| WATER | 87.3% |

In the foregoing formula the solvent serves as a vehicle for the active ingredient in the continuous phase causing the same to have molecular continuity and thereby provide an unbroken film; as distinguished from water solutions of water soluble active ingredients which would cause the resultant dispensant to be of a water beaded character with uneven distribution of the active ingredient.

EXAMPLE IX

The following formula also includes an active ingredient which is water soluble and which is adapted through the teachings of the present invention to provide a synthetic high temperature lubricant:

| | PERCENT BY WEIGHT |
|---|---|
| ACTIVE INGREDIENT | |
| Polyalkylene glycol | 5.0% |
| SOLVENT | |
| Isopar C* | 10% |
| DISPERSAL AGENT | |
| Cocodiethanolamide | 3.0% |
| WATER | 82% |

*Isopar C is a trademark of Exxon Corporation for an isoparaffinic hydrocarbon.

In this formulation the water soluble compound is carried by the organic solvent into the continuous phase thus providing uniform coverage of the lubricant.

Both of the foregoing Examples, VIII and IX, are exemplary of the effectiveness of the invention in improving the efficaciousness of certain water soluble chemicals.

EXAMPLE X

This example and the two succeeding provide typical formulae incorporating the present invention wherein the active ingredient is part of an emulsion. This particular example demonstrates a latex base paint:

| | PERCENT BY WEIGHT |
|---|---|
| ACTIVE INGREDIENT | |
| Latex Paint | 60% |
| DISPERSAL AGENT | |
| Cocodiethanolamide | 1.0% |
| WATER | 29% |
| SOLVENT | |
| Methylene Chloride | 10% |

The methylene chloride constitutes a relatively strong solvent for enhancing the bonding capabilities of the paint, that is for promoting the adhesion of the finish to unprimed surfaces. The addition of the solvent in this particular formula illustrates the capacity of the preparations of the present invention to integrate solvents for providing a specific property in the preparation which may serve its intended purpose without interfering with the inherent properties of the present preparation. Furthermore, in this example, the solvent is not a part, as it were, of the active ingredient as is shown in Examples III and VI above since it is more than likely incompatible with the latex paint which is fundamentally a closed system. Therefore, solvents utilized with such active ingredients are effectively brought into the preparation after the addition of the dispersal agent.

The foregoing Example, X, embodies an active ingredient in an emulsion so that the amount of dispersal agent will be less than 2.5% and follow the second general formula set forth above. With this particular formula it was found that 1% by weight of the dispersal agent would in addition to assuring attainment of the requisite energy level for dispersion also provide for the especial features sought in a good paint.

EXAMPLE XI

The following formula provides a hard surface polish and embodies an active ingredient which is also in an emulsion:

| | PERCENT BY WEIGHT |
|---|---|
| ACTIVE INGREDIENT | |
| Silicone Emulsion | 50% |
| (Mixture of General Electric SM2033* and SM2035) | |
| DISPERSAL AGENT | |
| Cocodiethanolamide | .05% |
| WATER | 49.5% |

*The foregoing identifications are utilized by General Electric Company of Waterford, New York to denote silicone emulsions of various viscosities.

The foregoing formula contains an active ingredient which is in a stable emulsion and with the dispersal agent being in minimum amount for providing the necessary energy for dispersion.

EXAMPLE XII

The following formula relates to a preparation of adhesive character:

| | PERCENT BY WEIGHT |
|---|---|
| ACTIVE INGREDIENT | |
| Polyvinyl Acetate Emulsion | 70% |
| DISPERSAL AGENT | |
| Cocodiethanolamide | 1.0% |
| WATER | 19% |
| SOLVENT | |
| Isoparaffinic Hydrocarbon | 10% |

In this example the active ingredient is in a stable emulsion so that the dispersal agent is in an amount substantially less than 2.5% in accordance with the above discussions. Also the solvent by reason of the closed system of the emulsion is introduced into the preparation after the incorporation of the dispersal agent, as in Example X above.

The characteristics and procedures for producing preparations according to the present invention are straightforward without requirement for complex instrumentation or equipment or concern for close control of environmental factors as all such production may be effected under ambient conditions. The active ingredient, whether the same be in pre-emulsified condition or otherwise, is intermixed with the indicated amount of cocodiethanolamide for thus forming the continuous phase and with the latter then having the water constituent blended therein. If a non-aqueous solvent is to be incorporated within the particular preparation as part of the active ingredient, the same is accordingly intermixed with the active ingredient and the cocodiethanolamide in the formation of the continuous phase. As pointed out hereinabove, if the particular solvent to be incorporated is incompatible with the active ingredient, then such solvent is added after the water or with or after the cocodiethanolamide if the active ingredient contains substantial water, as in fundamentally closed systems.

I claim:

1. A non-aerosolized preparation in the form of a water dispersion for providing an uninterrupted, continuous film consisting essentially of an active ingredient from the class consisting of water soluble and water insoluble compositions, said water insoluble compositions being initially non-pre-emulsified, a dispersal agent consisting of cocodiethanolamide within a range of 2.5% to 10% by weight of the preparation, said cocodiethanolamide being an amber liquid having a congealing point of approximately 6 degrees C., a specific gravity at 25 degrees C. of about 0.99, containing a maximum of about 3-14 percent free or unreacted fatty acid (as lauric acid) and having a pH value of 8-9 as a one percent dispersion in water, and being soluble in alcohols, glycols, ketones, esters, aromatic and aliphatic hydrocarbons, and chlorinated solvents, and also being dispersible in water at low concentrations of 1% to 2%, said active ingredient being within a range of approximately 0.05% to 80% by weight of the preparation, any requisite balance of said preparation being water, said preparation being non-emulsified.

2. A non-aerosolized preparation in the nature of a water dispersion according to claim 1 wherein said dispersion contains a continuous phase and an aqueous phase, said active ingredient and said dispersal agent comprising said continuous phase.

3. A non-aerosolized preparation in the nature of a water dispersion according to claim 2 wherein a non-aqueous solvent is provided in said continuous phase.

4. A non-aerosolized preparation in the nature of a water dispersion according to claim 1 wherein the active ingredient is from the class consisting of the active phase of water-base paints, waxes, greases, polysiloxanes, alkyl polysiloxanes, polyorganosiloxanes, polybutene, petroleum based hydrocarbon oils, synthetic oils, methoxy polyethylene glycols, water soluble resins, water soluble herbicides, and water soluble alkyl glycols and alkyl esters encompassing butoxylated and ethoxylated groups.

5. A non-aerosolized preparation in the form of a water dispersion as defined in claim 1 wherein the water is within a range of approximately 10% to 97.45% by weight of the preparation.

6. A non-aerosolized preparation in the form of a water dispersion as defined in claim 5 wherein the preparation includes a predilating agent compatible with the particular preselected active ingredient which agent is in an amount up to approximately 30% by weight of the preparation.

7. A non-aerosolized preparation in the form of a dispersion for providing an uninterrupted, continuous film consisting essentially of an active ingredient from the class consisting of water insoluble compositions which are pre-emulsified, a dispersal agent consisting of cocodiethanolamide within a range of 0.5% to 10% by weight of the preparation, said cocodiethanolamide being an amber liquid having a congealing point of approximately 6 degrees C., a specific gravity at 25 degrees C. of about 0.99, containing a maximum of about 3-4 percent free or unreacted fatty acid (as lauric acid) and having a pH value of 8-9 as a one percent dispersion in water, and being soluble in alcohols, glycols, ketones, esters, aromatic and aliphatic hydrocarbons, and chlorinated solvents, and also being dispersible in water at low concentrations of 1% to 2%, said active ingredient being within the range of approximately 1% to 99.5% by weight of the preparation, any requisite balance of said preparation being water, said preparation being non-emulsified.

8. A preparation according to claim 7 wherein the pre-emulsified active ingredient is in a stable emulsion.

9. A preparation in the nature of a water dispersion according to claim 7 wherein said active ingredient is pre-emulsified in an unstable emulsion and said cocodiethanolamide is in a quantity sufficient within the stated range to exceed stabilization of said active ingredient unstable emulsion by at least 0.5% by weight of the preparation.

10. A non-aerosolized preparation in the form of a water dispersion according to claim 7 wherein the water is in an amount up to approximately 98.5% by weight of the preparation.

11. A non-aerosolized preparation in the form of a water dispersion according to claim 10 wherein the preparation contains a non-aqueous solvent in an amount up to approximately 30% by weight of the preparation.

12. A non-aerosolized preparation in the form of a water dispersion according to claim 7 wherein the active ingredient is the active phase of a water base paint and the water is in an amount up to approximately 98.5% by weight of the preparation.

13. A non-aerosolized preparation in the form of a water dispersion according to claim 7 wherein said active ingredient is from the class consisting of waxes, greases, polysiloxanes, alkyl polysiloxanes, polyorganosiloxanes, polybutene, petroleum based hydrocarbon oils, and synthetic oils.

14. A non-aerosolized preparation in the form of a water dispersion for providing an uninterrupted, continuous film consisting essentially of an active ingredient from the class comprising water soluble compounds consisting of water soluble herbicides, water soluble alkyl glycols and alkyl esters encompassing butoxylated and ethoxylated groups, a dispersal agent consisting of cocodiethanolamide within a range of 2.5 to 10% by weight of the preparation, said cocodiethanolamide being an amber liquid having a congealing point of approximately 6 degrees C., a specific gravity at 25 degrees C. of about 0.99, containing a maximum of about 3-4 percent free or unreacted fatty acids (as lauric acid) and having a pH value of 8-9 as a one percent dispersion in water, and being soluble in alcohols, glycols, ketones, esters, aromatic and aliphatic hydrocarbons, and chlorinated solvents, and also being dispersible in water at low concentrations of 1% to 2%, said active ingredient being within the range of approximately 0.05% to 80% by weight of the preparation, and water within the range of approximately 10% to 97.45% by weight of the preparation.

15. A non-aerosolized preparation in the nature of a water dispersion as defined in claim 14 wherein a non-aqueous solvent in an amount up to approximately 30% by weight of the preparation is included.

* * * * *